(12) United States Patent
Matheis et al.

(10) Patent No.: US 11,141,516 B2
(45) Date of Patent: Oct. 12, 2021

(54) PORTABLE GAS EXCHANGE DEVICE

(71) Applicant: Novalung GmbH, Heilbronn (DE)

(72) Inventors: Georg Matheis, Heilbronn (DE);
Tatjana Thumm, Oberboihingen (DE);
Michael Hildebrand, Mössingen (DE);
Nektarios Panagias, Reutlingen (DE);
Dirk Stingel, Tieringen (DE); Reinhold Beuter, Rangendingen (DE)

(73) Assignee: Novalung GmbH, Heilbronn (DE)

( * ) Notice: Subject to any disclaimer, the term of this patent is extended or adjusted under 35 U.S.C. 154(b) by 341 days.

(21) Appl. No.: 15/571,978

(22) PCT Filed: May 9, 2016

(86) PCT No.: PCT/EP2016/000752
§ 371 (c)(1),
(2) Date: Nov. 6, 2017

(87) PCT Pub. No.: WO2016/177477
PCT Pub. Date: Nov. 10, 2016

(65) Prior Publication Data
US 2018/0140764 A1 May 24, 2018

(30) Foreign Application Priority Data

May 7, 2015 (EP) ..................................... 15001370

(51) Int. Cl.
*A61M 1/16* (2006.01)
*B01D 63/02* (2006.01)

(52) U.S. Cl.
CPC ... *A61M 1/1698* (2013.01); *A61M 2205/3666* (2013.01); *A61M 2205/42* (2013.01);
(Continued)

(58) Field of Classification Search
CPC ...... A61M 1/1698; A61M 1/26; A61M 1/262; A61M 1/265; A61M 1/267
See application file for complete search history.

(56) References Cited

U.S. PATENT DOCUMENTS 3,927,981 A    12/1975   Viannay et al.
4,610,656 A *   9/1986   Mortensen .......... A61M 1/3621
                                                                                                     128/DIG. 3
(Continued)

FOREIGN PATENT DOCUMENTS

EP          0183250 A2    6/1986
JP         2015039478 A    3/2015
(Continued)

OTHER PUBLICATIONS

Mehlhorn U. et al: "Lifebridge: A portable, modular, rapidly available "plug-and-play" mechanical circulatory support system", The Society of Thoracic Surgeons, Elsevier 2005; vol. 8, pp. 1887-1892.

(Continued)

*Primary Examiner* — Philip R Wiest
(74) *Attorney, Agent, or Firm* — Dinsmore & Shohl LLP

(57) ABSTRACT

The invention relates to a portable gas exchange device for gas exchange of at least one gas from a liquid to a fluid. The gas exchange device comprises a first gas exchange section, for passage of a fluid, and a second gas exchange section for passage of a liquid enriched with a first gas, wherein the fluid has a lower concentration of the first gas than the liquid. A pumping system for transporting a first fluid with a lower concentration of a first gas in the first gas exchange section, in particular in a first fluid circuit, is also configured in the gas exchange device. In a mixing chamber configured in the (Continued)

gas exchange device, the first gas exchange section and the second gas exchange section adjoin one another via a wall designed such that at least the first gas can pass through. A housing serves as the common receptacle at least of the pumping system and the mixing chamber.

25 Claims, 2 Drawing Sheets

(52) U.S. Cl.
CPC ............... *A61M 2205/8206* (2013.01); *A61M 2209/088* (2013.01); *B01D 63/02* (2013.01)

(56) References Cited

U.S. PATENT DOCUMENTS

| | | | | |
|---|---|---|---|---|
| 5,308,314 | A * | 5/1994 | Fukui | A61M 1/1698 |
| | | | | 128/DIG. 3 |
| 7,541,000 | B2 * | 6/2009 | Stringer | F04D 9/006 |
| | | | | 422/45 |
| 2002/0161349 | A1 * | 10/2002 | Allers | A61M 1/369 |
| | | | | 604/500 |
| 2008/0027368 | A1 | 1/2008 | Kollar et al. | |
| 2009/0081079 | A1 * | 3/2009 | Johns | A61M 1/1678 |
| | | | | 422/46 |
| 2010/0101657 | A1 * | 4/2010 | Morley | A61M 1/1698 |
| | | | | 137/14 |

FOREIGN PATENT DOCUMENTS

| | | |
|---|---|---|
| WO | 9947189 A1 | 9/1999 |
| WO | 2013041950 A1 | 3/2013 |
| WO | 2014012536 A1 | 1/2014 |
| WO | 2014177944 A2 | 11/2014 |

OTHER PUBLICATIONS

Tatsumi E. et al: "Development of an ultracompact integrated heart-lung assist device", Artificial Organs 23 (6):518-523, 1999 Blackwell Science, Inc.

Wang D et al: "An ambulatory pulmonary and right heart assist device (OxyRVAD) in an ovine survival model", Journal of Heart and Lung Transplantation, vol. 26, No. 10, pp. 974-979; 2007, International Society for Heart and Lung Transportation.

Tsukiya T. et al. "Design progress of the ultracompact integrated heart lung assist device—Part 1: Effect of vaned diffuser on gas-transfer performances", Artificial Organs 27(10):907-913; Blackwell Publishing, Inc., 2003.

* cited by examiner

PORTABLE GAS EXCHANGE DEVICE

CROSS-REFERENCE TO RELATED APPLICATIONS

This application is the U.S. national stage of PCT/EP2016/000752 filed May 9, 2016, which claims priority of European Patent Application 15001370.4 filed May 7, 2015 of which is hereby incorporated by reference in its entirety.

FIELD OF THE INVENTION

The invention relates to a gas exchange device—in particular, for treatment of a biological liquid.

BACKGROUND OF THE INVENTION

A gas exchange device may be a gas supply or gas removal device in which one or more gases may pass from one medium into another medium, or a device which enables the exchange of one or more gases between two media. Such devices are used in chemistry, biotechnology, and medicine. An important intended use in medicine is the enrichment of a biological liquid—in particular, blood—with oxygen, and/or the removal (thus depletion) of carbon dioxide from the liquid—especially, blood. Such measures are necessary when treating various pulmonary diseases, for example. Furthermore, such measures may also be necessary in case of acute respiratory failure, for example, as well as for the replacement of a lung; while bypassing a lung with an extracorporeal circuit; to a different extent, in case of mechanical cardiac support; and to enable operating on stopped hearts.

The only long-term effective therapy option at present for patients with end-stage functional pulmonary disease is a lung transplant. There is no other medical solution for permanently replacing the function of the lungs. For patients who suffer from chronic pulmonary diseases and are not being considered or not immediately being considered for a lung transplant, there is, therefore, a need for artificial lung replacement methods.

In order to make possible such a lung replacement method, what are known as blood gas exchangers are known from the prior art.

A blood gas exchanger, also designated as an oxygenator or artificial lung, is used either for complete, temporary takeover of the lung function during an open-heart operation, or as a complete or partial long-term support of the lungs in the intensive care unit. The primary function of a blood gas exchanger consists in delivery of oxygen to the blood (oxygenation) and in the uptake of carbon dioxide from the blood (decarboxylation). For example, the gas exchange occurs by means of hollow fiber membranes, around which blood flows in the extracorporeal gas exchanger, while oxygen-rich or carbon dioxide-poor gas is simultaneously directed through the inside of the fibers. Due to the difference in concentration, oxygen or carbon dioxide may diffuse in respectively opposite directions through a semi-permeable membrane—typically, a gas-permeable membrane. The membranes used for this—what are known as membrane plates—can be obtained commercially.

In addition to application in oxygenation and decarboxylation, in some therapy uses, it is already sufficient to perform only a decarboxylation. This is thereby what is known as an extracorporeal reduction of $CO_2$ (ECCO$_2$R). For this, blood is continuously removed via a venous access of the patient, pumped extracorporeally through a blood gas exchanger, cleaned there of $CO_2$, and venously supplied again to the patient.

Systems and, in particular, pumps that are common in the prevalent ECCO$_2$R applications, and in what is known as extracorporeal membrane oxygenation (ECMO), are used that, as part of a heart-lung machine within the scope of open-heart cardiac surgery procedures, may also predominantly take over the pumping function of the heart in cardiac surgery during circulatory arrest. These pumping systems are designed and dimensioned for the necessary volume flows of up to 6 l/min for the sufficient oxygenation of the blood during circulatory arrest.

For gas exchange in such blood gas exchangers, oxygen is typically used, which is available in any hospital, either directly via a wall connection or via oxygen bottles. The oxygen is then supplied via a controllable gas diaphragm to the blood gas exchanger.

Pumping systems for ECCO$_2$R applications are, in principle, operated on a stationary power grid. In the event of an emergency, e.g., a power failure, an emergency power supply may be maintained by means of battery operation. Since medical facilities normally possess emergency power generators, however, a battery operation is time-limited and, with the known gas exchange devices, is normally not designed for long-term operation or mobile operation. A known blood gas exchange system, which, indeed, possesses a mobile power supply, nonetheless requires a (for example, rollable) carrier device to travel with it, as well in order to carry along the plurality of different, in part cumbersome, components of the blood gas exchanger.

Due to its size, weight, and the arrangement of connections for blood-carrying tubes, for example, the use of the known gas exchange devices is therefore essentially limited to stationary applications in which the patient (conscious or sedated) is lying in bed. Patients with chronic pulmonary diseases that are reliant on these known gas exchange devices are thus severely limited in their mobility. This does not just significantly reduce the quality of life of the patients. Modern therapy approaches that stress a mobilization of the patient cannot be implemented.

The known gas exchange devices are thereby, in particular, also too voluminous and too heavy to be worn on the body by a patient, in particular over a longer period of time. In the event of chronic pulmonary illnesses, even therapy approaches that aim merely to relieve the lungs, and not completely replace them, therefore require a stationary application.

SUMMARY OF THE INVENTION

The present invention is based upon the aim of providing an improved pumping system or an improved gas exchange device, in order to overcome at least one of the disadvantages of the known system and to enable a mobile application. In particular, it is an aim of the present invention to reduce space requirements and weight of a pumping system in a gas exchange device. It is, additionally, an aim to provide a gas exchange device that may be transported by a patient, even over a longer period of time, preferably directly on the patient's body.

This aim is achieved via a gas exchange device according to claim 1. Advantageous developments of the invention are the subject matter of the dependent claims.

A gas exchange may be subject to the convective and diffusive exchange of substances. Preferably, gas exchange is diffusive and is determined by the difference in the gas concentration on both sides of a membrane. For the present invention, this means that, in a system made up of different coupled fluids, e.g., a liquid and a gas, an equilibrium of the respective—gaseous—components of the fluid is established. If a gas containing a very low proportion of a gas in a liquid with an increased proportion of this gas now circulates around this liquid, the gas proportion of this specific gas passes from the liquid into the circulating gas until a concentration equalization has occurred. If the gas flow enriched with the gas is replaced by a gas mixture depleted of the gas, the concentration ratio between liquid and circulating gas mixture remains invariably high, and a continuous delivery of gas from the liquid occurs.

According to one aspect of the present invention, a portable gas exchange device is provided for gas exchange of at least one gas from a liquid with a fluid. The gas exchange device has a first gas exchange section for passage of a first fluid and a second gas exchange section for passage of a liquid enriched with a first gas. The gas exchange device additionally has a pumping system that is designed at least for the transport of the first fluid with a low concentration of a first gas into the first gas exchange section. In the first gas exchange section, a first fluid circuit may thereby be formed, through which the first fluid flows. In a mixing chamber of the gas exchange device, the first gas exchange section and the second gas exchange section adjoin one another and are separated by a wall designed to be permeable at least to the first gas. In addition to this, the gas exchange device has a housing for accommodating at least the pumping system and the mixing chamber. The accommodation thereby preferably takes place together in the same housing.

The housing preferably has a maximum internal chamber volume of preferably 9,500 cm$^3$, given a preferred maximum average depth of 15 cm and given a preferred average total value of, altogether, at most, 65 cm for height and width. The average height or the average width hereby preferably amount to 40 cm at most. The depth thereby preferably amounts to ¼ to ⅛ of the sum value of the average height and the average width taken together, such that the housing achieves a compact to flat character. Essentially all functional units of the gas exchange device are integrated into this compact housing, whereby it is made possible for a patient to comfortably carry the gas exchange device on his body.

What is thus to be understood here by a "low concentration" is that the fluid provided in the first gas exchange section is provided with a lower, preferably distinctly lower, concentration of the gas than the liquid in the second gas exchange section.

In such a pumping system, the first and a second fluid circuit may at least partially adjoin one another and be separated by a selectively permeable wall. The second fluid circuit is thereby preferably designed as part of the second gas exchange section. The pumping system has at least one pumping device that is designed for the transport of a first fluid with a low concentration of a first gas into the first gas exchange section or into the first fluid circuit. In addition to this, the pumping system may have a mobile power supply. The power supply may thus enable an autarkic operation of the pumping system.

A separation between two fluids that have the same state of aggregation or different states of aggregation is also designated as a "selectively permeable wall" in the sense of the invention. This separation preferably allows a passage of predetermined components, in particular specific gas molecules. It may thereby, in particular, be a wall that is permeable to blood gases, for example carbon dioxide or oxygen. It is understood that, depending upon the specific field of use, the walls may also be permeable to additional or different gases or fluids, or to components of these.

In the sense of the invention, what is to be understood as a fluid circuit is an arrangement that allows the passage of a fluid, i.e., a liquid or a gas or a gas mixture, from an inflow or inlet to an outflow or outlet. However, it does not thereby need to be a closed circuit. Rather, in the sense of the invention, an inlet and an outlet may be arranged to be spatially separate from one another, wherein, in the sense of the invention, a circuit may nevertheless be spoken of.

For example, a mobile power supply in the sense of the invention may have a battery—preferably, a rechargeable battery, e.g., a lithium ion rechargeable battery. The mobile power supply may advantageously have at least two separate and separately removable batteries—preferably, rechargeable batteries. In this instance, one of the rechargeable batteries may be charged outside of the device while the corresponding other rechargeable battery takes over the supply of power to the pumping system. The power supply may thereby be designed so that an exchange of the batteries is possible while the system remains functional ("hot swapping"). The battery or batteries may also serve as the power supply of a control unit of the pumping system, or as the power supply of the entire gas exchange device according to the invention or of its control unit.

Common systems, in particular also for extracorporeal reduction of $CO_2$, are stationary systems that are, in principle, not suitable for mobile use, and, in particular, not for use while they are carried along with or even worn by a patient. These known systems accordingly neither are provided with a mobile power supply, nor are components included that may be operated long-term without a direct mains connection. According to the invention, via the provision of a mobile power supply, it is made possible that a gas exchange may take place between a first fluid—example, a biological fluid such as blood—and a second fluid—for example, a gas such as carbon dioxide—said gas exchange taking place independently of the location. The fluid may thereby, for example, be a gas or gas mixture such as oxygen, ambient air, ambient air enriched with oxygen, or ambient air depleted of carbon dioxide or other components, and others. A pumping operation, and thus a gas exchange, may therefore take place according to the invention over the long term even when a patient is not connected to a stationary, mains-coupled power supply.

Preferred embodiments of the device according to the invention serve exclusively for the extracorporeal reduction of the carbon content in blood. However, the developments and advantages depicted here also apply to the same extent to systems that, as an alternative or in addition to a gas depletion of the liquid, e.g., the aforementioned decarboxylation, may produce a gas enrichment in the liquid—for example, an oxygenation of blood. Systems for oxygenation or systems for enrichment by and/or depletion of other substances, gases, or molecules are also to like extent, in principle, encompassed by the concept according to the invention of providing a portable gas exchange device.

In particular, the provision of a housing in which the pumping device and the mixing chamber can be accommodated—preferably, together with the corresponding supply and discharge lines—allows a compact arrangement of the necessary components for extracorporeal gas exchange such that a device may be achieved that can be carried by a patient, which thus does not need to be carried by means of auxiliary medical equipment or by accompanying persons. According to the invention, the gas exchange device in the housing may, in particular, also be carried directly on the body of a user. For this, the gas exchange device and, in particular, the housing may also have suitable retention means for attachment to a patient's body, clothing, or pockets.

In some developments of the invention, the first gas exchange section—in particular, the first fluid circuit—has a particle filter. The particle filter is preferably formed at the inlet side—in particular, in, at, on, or in front of a suction or connection section of the first fluid circuit. The particle filter thereby enables a filtering of the first fluid. The first fluid may thereby, in particular, have, essentially, ambient air, oxygen, or a mixture of ambient air and oxygen. It is understood that the most varied gases and gas mixtures can be used in the same manner with the gas exchange device according to the invention. Via the provision of a particle filter in the first fluid circuit, it may be avoided that foreign bodies—for example, dust, particulates, or other suspended particles—arrive in a region of the gas exchange device in which a gas exchange takes place between the first fluid circuit and the second fluid circuit. Clogging of the actual gas exchange region—in particular, in the mixing chamber—between the fluid circuits may thus be reduced or prevented. This is advantageous, in particular, in an instance in which the first fluid has ambient air or is comprised at least to a significant degree of ambient air that is autarkically pumped from the environment by the gas exchange device.

What is thus designated as "inlet-side" is a section of the affected (here, the first) fluid circuit that is formed to one side of the inlet, i.e., prior to a gas exchanger in the upstream direction of the fluid circuit. This comprises the inlet in and of itself, but also, for example, a line section that conducts the first fluid from the inlet to the gas exchanger. The inlet may thereby be designed as a suction section or a fluid connection—for example, a gas connection. For example, air may be drawn from the environment of the suction section into the pumping system by means of a suction connection. A fluid connection may allow the direct connection for additionally, separately, or optionally supplying an accompanying fluid. In this way, the suctioned air may, for example, be enriched with a desired component—for example, oxygen.

Analogously, "outlet-side" designates a section of the corresponding fluid circuit that is designed downstream of a gas exchanger. This comprises an outlet or an outlet connection, just as with a line section leading to the outlet. The gas conducted through the outlet connection may be supplied again, at least in part, to the fluid circuit at the inlet section. Particularly with cold ambient temperatures, this may reduce energy for heating the supplied or suctioned air.

What is designated as "ambient air" in the sense of the invention is thus a typical air mixture of nitrogen, oxygen, carbon dioxide, and additional components, which typically also qualifies as breathable air. In particular, the term "ambient air" according to the invention designates a gas mixture of the sort that has a carbon dioxide content of typically less than 0.5-1 vol %—in particular, of approx. 0.04 vol %.

The gas exchange device according to the invention—in particular, the pumping system—may have a first pump (20) for pumping the first fluid—preferably a gas, e.g., ambient air.

The gas exchange device according to the invention—in particular, the pumping system—may have a second pump for pumping a liquid—preferably, a biological liquid—through the second gas exchange section—preferably, a second fluid circuit. In this way, it may be enabled that an improved transport of the second liquid—which may, in particular, be a biological liquid such as blood—can take place via the pumping system and components connected thereto. In this way, insofar as the second liquid is the blood of a patient, a pumping capacity of the heart of the patient may be supported, or the stress on the heart of a patient may at least be reduced. In addition to this, a flow through the second gas exchange section may take place uniformly and independently of a heartbeat.

In some developments of the invention, the first and/or the second pump of the pumping system may have a control means for controlling the flow rate of the respective fluid transported by the pump. A depletion rate of the first gas may thereby be adjusted via corresponding activation of the first and/or the second pump. Concretely, this may mean that a flow rate of the first pump is increased in the event of an increased gas proportion in the liquid—for example, an increased carbon dioxide enrichment in the blood. The difference in concentration of the first gas in the liquid and in the suctioned gas may thereby be increased, and an improved carbon dioxide depletion may, in the present example, occur. An increased carbon dioxide enrichment in the liquid may be reacted to, so to speak, by increasing the pumping capacity of the second pump. With increased pumping capacity, an increased liquid volume may be transported by the gas exchanger. For example, this may be necessary when the patient is physically active.

It is understood that the first and second pumps may be activated independently of one another, or also jointly—in particular, simultaneously. This may also make it possible that, from each liquid flow volume—in particular, blood flow volume—the ratio of gas to blood flow is optimized by the gas exchanger. This may reduce an invasiveness due to an external gas exchange device, e.g., in that a vascular access that has an optimally small lumen may be used on a patient. For example, this may be realized, via what is known as a master-slave operation of the pumping system or of the fluid circuits, with diverse sensors. Accordingly, a flow rate—for example, a maximum and/or minimum and/or optimal flow rate—of one of the pumps may be adjustable as a function of a setting or a delivery rate—for example, a maximum and/or minimum and/or set delivery rate—of the corresponding other pump. It is understood that the relevant corresponding pumping capacities of the first and second pumps may also be stored in a memory unit of a control unit—for example, as a function of a lumen of a vascular access. For example, a partially or fully automatic adjustment of the pumping parameters may take place in this manner. This may increase the operating comfort of the device. In addition to this, an improved—in particular, an optimal—gas exchange capacity may be achieved in case of low blood flow—in particular, for the lowest possible blood flow.

The flow rate of the first pump may thereby be adjustable in a range of between 1-12 l/min, preferably between approx. 1-8 l/min. This may, in particular, be the case if the first pump is provided and designed for pumping a gas. In alternative embodiments, it is conceivable that the fluid in the first fluid circuit is a liquid—for example, a liquid enriched with or depleted of a gas. A pumping volume may then accordingly be adjustable in other adequate ranges.

In particular, the first pump is a pump having a power-to-weight ratio of less than 30 kg/KW at a pump weight of at most 0.5 kg, preferably at most 0.3 kg. By the use of a pump having a power-to-weight ratio of less than 30 kg/KW at a maximum pump weight of at most, 0.5 kg, preferably at most 0.3 kg, a compact and light design of the gas exchange device may be achieved that enables the gas exchange device to be carried by a person without expenditure of energy.

In some embodiments of the present invention, the flow rate of the second pump is less than 4 l/min, and preferably less than 2 l/min. The flow rate of the second pump is thereby preferably controllable and/or adjustable. The flow rate of the second pump is thereby preferably 0.2 to 2.0 l/min. The flow rate of the second pump is advantageously adjustable to between approx. 0.2-1.5 l/min, preferably between approx. 0.3-1 l/min. The maximum achievable flow rate of the second pump is thereby also, advantageously, less than 4 l/min, preferably less than 2 l/min and in particular at most 1.5 l/min. Such a pump, which has significantly lower maximum flow rates than the known pumps provided for this intended purpose, may allow a significant reduction in the structural size, the structural weight, or even the power consumption. The longer pumping capacities that result from this may increase mobility of the pumping system. The provision of pumps having lower pumping capacity according to the present invention may additionally also entail a reduction in the size of the pumps used. This may allow the weight of the pumping device, and thus of the entire system, to be reduced. This may facilitate transport of the entire pumping system, and, in particular, may enable portability directly on the body of a patient.

The second pump is, in particular, a pump having a power-to-weight ratio of less than 25 kg/KW at a pump weight of, at most, 0.7 kg—preferably, at most, 0.5 kg. Through the use of a pump having a power-to-weight ratio of less than 25 kg/KW and a maximum pump weight of 0.7 kg—preferably, at most, 0.5 kg—a compact and light design of the gas exchange device may be achieved that enables the gas exchange device to be carried by a person without expenditure of energy.

The reduction in the pump size may additionally enable the pumping device to be accommodated more easily together with a gas exchange device in a common housing. This may further improve portability of the system and increase comfort for the respective wearer.

The housing may thereby have, for example, a housing insert that is designed with receptacle recesses for various components of the gas exchange device. In particular, the housing insert may be of one piece. The housing or the housing insert may, for example, have a foamed material or a dead-mold cast material. The housing or the housing insert may thereby be provided, e.g., via provision of corresponding moldings in the housing or the housing insert, such that a positive-fit receptacle for the components of the gas exchange device is made possible. In some embodiments, the housing may be designed as one piece with the housing insert.

The housing or the material of the housing insert may have a sound-insulating and/or thermally-insulating material. In addition to this, the material of the housing insert may have a shock-resistant and/or water-repellent material.

The housing may enable a compact, secure, and maintenance-friendly accommodation of the essential components of a gas exchange system. In this way, a portable gas exchange device that can be carried by a patient may be provided.

In advantageous developments of the invention, the ratio of the flow rate of the first pump to the flow rate of the second pump is in a range of between 4:1 and 6:1. The flow rate ratio is preferably approx. 5:1. An optimized $CO_2$ reduction rate may be achieved or set via such an adjustment of the flow rates of the respective pumps.

In a development of the invention, a drive of the first pump and/or a drive of the second pump may be arranged or positioned in the gas exchange device such that waste heat of the drive of the first and/or second pump warms an inlet-side section of the first fluid circuit. For this, the first and/or the second pump may have attachment means that enable such an arrangement in the gas exchange device. For example, at least one supply flow line may be arranged in spatial proximity to at least one first pump, one second pump, or also a first pump and a second pump. An arrangement in immediate proximity to one or both of the drives of the first and second pumps may also take place. It is also conceivable that an outlet line of the first fluid warmed by the gas exchange process is directed along or, in sections, around the supply flow line of the first fluid. In this way, a warming of the suctioned first fluid may in turn take place. Via the warming of the supply flow line or gas line, the advantage results that no condensation water may form which, as small droplets, might partially close the hollow fibers in the oxygenator. A partial closure of the gas exchanger or oxygenator may dramatically reduce the effectiveness of the gas exchange, which is why known oxygenators therefore should be aerated several times per day.

A device for active temperature control is preferably provided that has at least one temperature sensor arranged in the housing, at least one ventilating fan, and a governor device. By means of the device for active temperature control, in the operating state, the internal temperature in the housing may, for example, be adjusted in a temperature range of 34 to 42° C.—preferably, in a temperature range of 35 to 38° C. The waste heat of the pump or pumps is thereby distributed via the air current in the housing to warm the components, and excess heat may be delivered to the environment via the housing opening. A tempering of the suctioned first fluid may hereby also be achieved in a simple manner. The governor device is thereby preferably integrated into the control device of the gas exchange device, wherein the governor device controls the ventilating fan with respect to flow velocity and flow direction using the measurement data of the at least one temperature sensor.

It is also advantageous if the ventilating fan is arranged between a pump and a housing opening—preferably, at a short distance (less than 3 cm) from both the pump and the housing opening—whereby rapid heat dissipation from the housing is enabled.

Via such an arrangement of the pumps, energy can be saved if a warming of the first fluid prior to a gas exchange is desired. This may extend the battery run time. In addition to this, a gas exchange rate may be improved with a warmed fluid during the gas exchange.

A noise suppressor for dampening noise emission due to the ejection of the first fluid may be provided at the outlet side of the first fluid circuit—in particular, at an outlet section. A noise level of the pumping system may thereby be reduced. This may reduce noise disturbance—in particular, with the mobile use of the pumping system—and increase the usage comfort.

In some developments, the pumping system comprises at least either a pressure sensor and/or a gas flow sensor and/or an air bubble sensor. This may improve control of the pumping system and error detection. The reliability may thereby be improved, and the range of application of the pumping system may thereby be increased. The first fluid may thus be reliably used exclusively for depletion of a component of the second fluid, without an enrichment with a different component simultaneously taking place.

The first pump of the pumping system may, advantageously, be designed as a suction pump. This may, on the one hand, allow smaller, lighter, and quieter pump components with correspondingly lower power consumption to be used for the pumping system. In addition to this, by means of a suction pump, it may reliably be prevented that components (in particular, gas components) of the first fluid pass into the second fluid due to the suction principle.

The portable gas exchange device may have an autarkic fluid supply for supplying the gas exchange device with fluid. In particular, ambient air may thereby be provided by the autarkic fluid supply. The use of ambient air may therefore, in particular, be advantageous, since carbon dioxide content in the ambient air is much lower than carbon dioxide content in, for example, venous blood. A carbon dioxide depletion in blood that flows through the second fluid circuit may thus be produced merely by flows of ambient air through the first fluid circuit. Accordingly, if an $ECCO_2R$ application is indicated, no heavy compression bottles for supplying gas to the gas exchange device must be carried along by a patient. In this instance, it is sufficient to draw ambient air and stream it through the first fluid circuit. This may further increase portability and mobility for a patient.

In this context, "autarkic" is to be understood such that an external supply of gas—for example, via carried gas bottles—is not necessary. Rather, a supply with gas takes place independently of a carried gas supply. It is understood that, in some embodiments of the invention, a gas supply can nevertheless be connected to the gas exchange device, e.g., an oxygen pressure bottle—preferably, an oxygen pressure bottle of small size. It is additionally conceivable that a mixed operation from an autarkic gas supply and a carried gas supply can be implemented. Control of the operation, or of the mixed operation, may thereby also take place—preferably, automatically—on the basis of sensor results or blood gas measurements. A combination of these gas supplies may also be provided temporarily.

The first or second gas exchange section of the gas exchange device may thereby essentially coincide with the first or second fluid circuit of the pumping system. To this extent, the pumping system with the first and second fluid circuits may be provided as an independent component. Alternatively, the first and second fluid circuits may be fixed components of the gas exchange device, and thus may form components of the first or second gas exchange section. In addition to this, it is also conceivable that the first and second fluid circuits are directly integrated into the housing of the gas exchange device and are inseparably connected to this. This may also apply to only one of the fluid circuits—for example, to the first fluid circuit.

The portable gas exchange device according to the invention—in particular, with an autarkic fluid supply—allows mobile use of a gas exchange device. This may have significant advantages for users—for example, for patients who depend upon an extracorporeal gas exchange of blood. The extracorporeal gas exchange may, advantageously, also take place over the long term with the device according to the invention.

In some developments, the portable gas exchange device has a control unit that is designed to control the flow rate of at least one pump of the pumping unit, i.e., of the first and/or second pump of the pumping system. The control unit for the first and/or second pump of the gas exchange device may thereby advantageously be designed to be integral with a control unit for the entire gas exchange device. This may allow a flexible adaptation of the pumping capacities, and thus also an adaptation to individual relationships or requirements of a user of the gas exchange device.

In some developments of the invention, the wall of the portable gas exchange device between the first gas exchange section and the second gas exchange section is designed so that this is additionally permeable to at least one second gas. In alternative embodiments, the gas exchange device and/or the pumping system may also have a third gas exchange section or a third fluid circuit wherein an additional fluid may flow. This additional fluid may, for example, be oxygen or contain an increased oxygen content in comparison to ambient air. It is also conceivable that the third fluid has more complex components—for example, biochemically reactive substances such as medicines or the like. In particular, the administration of, for example, anesthetic gases during an operation may also be enabled by means of a device according to the invention.

The portable gas exchange device may comprise at least one monitoring means having at least either a pressure sensor and/or a blood flow sensor and/or an air bubble sensor. The at least one monitoring means may thereby, in particular, also be connected to the control unit. The control unit thereby preferably has at least one indicator for the display of a measurement value and/or for the presentation of a malfunction of the gas exchange device. The control unit preferably comprises a display unit for the presentation of information and/or malfunctions, as well as diverse operating parameters. The monitoring means of the gas exchange device may thereby also be designed integrally with the monitoring means of a pumping system provided in the gas exchange device. The monitoring means may allow an improved review of the functionality of the gas exchange device or of individual components. In particular, the provision of a monitoring means may allow a control loop to be provided in the gas exchange device, or also in the pumping system. A reliable supply with fluid in the gas exchange device may thus be ensured.

The blood flow sensor or air bubble sensor allows the detection of blood flow via the gas exchange device. In this way, a function of the gas exchange device may be monitored. The air bubble sensor detects air bubbles that are present in the liquid—in particular, in the blood. This may in turn increase the safety of the device—for example, in that it is prevented that air bubbles be transported from the extracorporeal region into a blood circulation in the body. In specific embodiments, only one blood flow sensor or only one air bubble sensor, or respectively one blood flow sensor and one air bubble sensor, may also be provided separately from one another.

In developments of the invention, a respective redundant fluid circuit may be provided at the first and second, and also possibly at the third, fluid circuits. In case of failure of one of these circuits—in particular, in an instance in which medical measures cannot immediately be implemented on a patient dependent upon the gas exchange device—the redundant system may alone take over the function of the gas exchange. For this, a control or governing technique for adaptation of the flow rates of the respective pumps may automatically increase the corresponding flow rates of the redundant system.

In the same manner, an increase in the flow rates may, at least to a limited extent, counteract an efficiency reduction in the gas exchanger. Such an efficiency reduction may, for example, be the result if blood is conducted through a gas exchanger and blood components begin to adhere at the wall between the first and second fluid circuits, and thereby prevent a gas transport through the wall.

Moreover, it is possible to produce—again, at least to a limited extent—a reduction—for example, an automatic reduction—in one or both flow rates of the fluids, e.g., to a medically necessary minimum. This may be necessary in the event that the capacity of the power supply is too low, and a possibility for recharging is not immediately present.

In embodiments in which the gas exchange device has the pumping system according to the invention, it is understood that the power supply, in the form of one or more preferably rechargeable batteries, jointly feeds the pumping system, the control unit, and additional components to be supplied with current.

The control unit of the portable gas exchange device may be connected to the gas exchange device via power and/or data cables. A power supply of the control unit and of the gas exchange device in the control unit may thereby be provided. It is also conceivable that the power supply is provided in the housing of the gas exchange device, or that at least a portion of a power supply is provided in the housing of the gas exchange device. In such an instance, it is also conceivable that the control unit of the gas exchange device is connected wirelessly to said gas exchange device. For this, the control unit, as well as the gas exchange device, may have a transmission and/or reception unit. This may increase the comfort in the operation of the gas exchange device.

It is additionally conceivable that the control unit itself represents a modular system that comprises at least a base station and a portable control unit. The base station and the portable control unit may, in this instance, in turn be connected to one another wirelessly. In this way, data may be transmitted from the portable control unit to the base station, e.g., current pumping rates, temperatures of the fluids and/or vital parameters, and the like, insofar as these data are acquired. In addition to this, the base station may, for example, transmit control commands for controlling the gas exchange device to the portable control unit.

In this way, a movement radius of a patient may be increased. For example, a movement radius of 50 m or more relative to the base station may be enabled for a local data connection between the portable control unit and the base station.

Furthermore, at the control unit, a means may be provided that allows an attachment of the control unit to the portable gas exchange device. For this, at the gas exchange device, a complementary means may be provided so that, for example, an attachment section of the control unit engages with an attachment section of the gas exchange device, and may enable a reliable attachment of the gas exchange device. The attachment of the control unit may, for example, be provided at the housing of the gas exchange device. Alternatively, an attachment of the control unit to a carrier system of the gas exchange device may also be provided. In addition to this, an attachment of the control unit directly to the clothing of a patient may also take place. In addition to this, the attachment means of the control unit may also be provided for attaching the control unit to a support structure, e.g., to a patient's bed, or to a carrier system for medical devices in a hospital room.

In particular, the attachment means of the control unit may have a hook-shaped form that enables hooking the attachment means to a complementary receptacle section, or, for example, to a tube-shaped element or an outer contour of the housing of the gas exchange device. In addition to this, an attachment to a flat structure—for example, to a rolling chair back or the like—is conceivable. For this, the attachment means of the control unit may be designed with a spring pre-tensioning, so that a clamping due to the spring pre-tensioning of the attachment means provides a sufficient retention force for attaching the control unit. Moreover, the attachment means or an additional stand means may be designed and formed at the control unit such that said control unit may be set up on a support—for example, a table or a roll container or the like.

Insofar as a base station and a portable control unit are provided, the base station may have a connection section that is provided for accommodating or at least connecting the portable control unit. In this way, the portable control unit may be connected to the base station—for example, if a patient remains in proximity to the base station. For this, the base station may, in particular, have a charging device for charging the batteries provided in the portable control unit. The portable control unit may thus be charged—for example, during a rest phase of the patient—in particular, overnight—without operation of the gas exchange device needing to be interrupted.

BRIEF DESCRIPTION OF THE DRAWINGS

The invention, as well as advantageous developments thereof, will now be explained by means of certain exemplary embodiments represented in the attached drawings, in which equivalent features are given the same reference numbers. The following is shown.

DETAILED DESCRIPTION OF THE INVENTION

Figure 1:
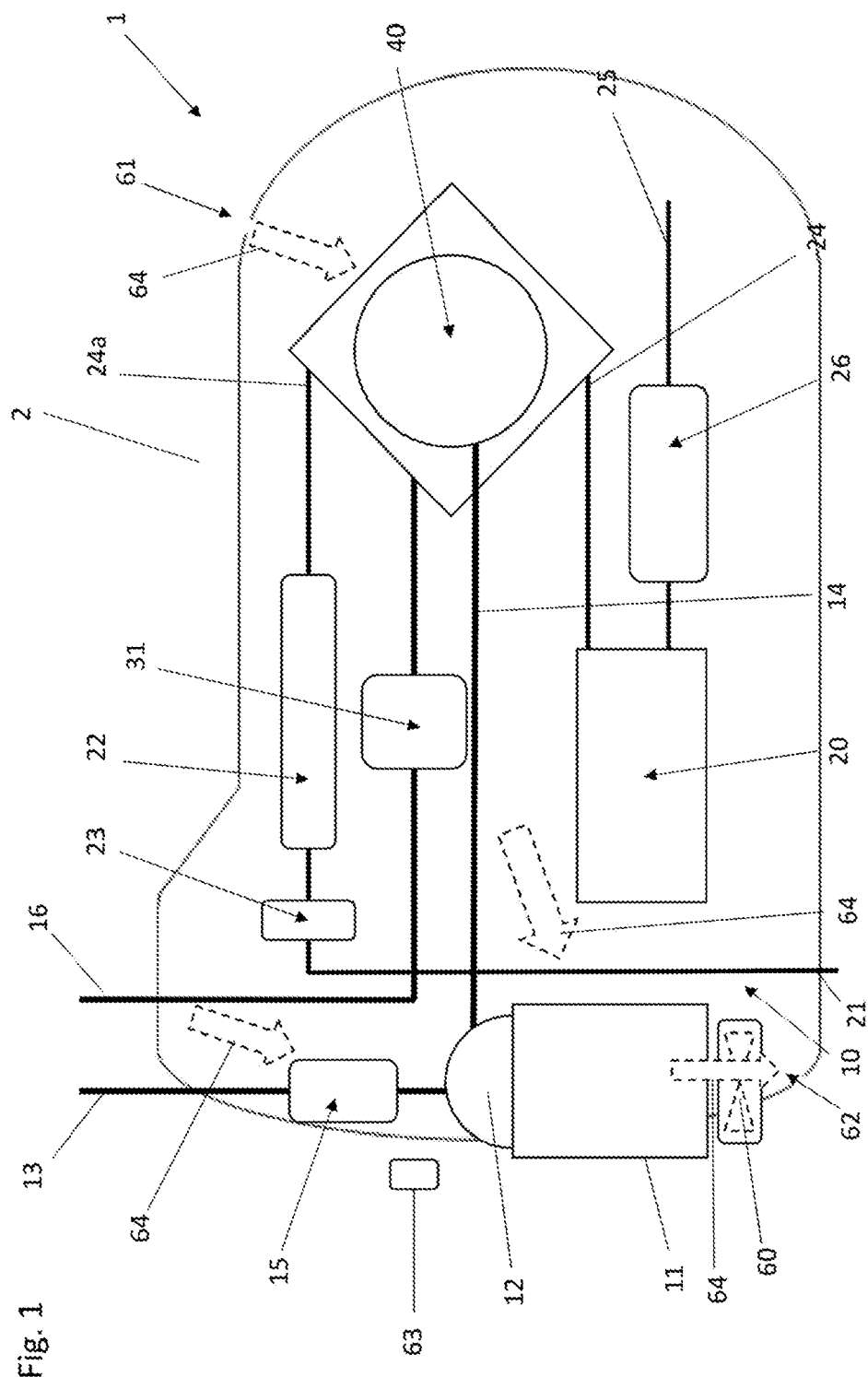
FIG. 1 is a schematic view of a portable gas exchange device according to an embodiment of the invention, having a pumping system.

FIG. 1 shows a portable gas exchange device 1 according to an embodiment of the invention. The gas exchange device 1 serves for gas exchange between a first fluid and a second fluid. In order to enable a gas exchange between the fluids, a pumping system 10 is provided in the gas exchange device 1.

The pumping system 10 has a first pump 20 that is designed as a gas pump in the embodiment shown in FIG. 1. A second pump 11 presented in FIG. 1 is, in the present case, a liquid pump that is designed to pump a biological liquid—in particular, blood. The first pump 20 thereby has a power-to-weight ratio of less than 30 kg/KW, given a pump weight of, at most, 0.5 kg—preferably, at most, 0.3 kg—whereas the second pump 11 has a power-to-weight ratio of less than 25 kg/KW, given a pump weight of, at most, 0.7 kg—preferably, at least 0.5 kg.

The second pump 11 is also designated as a blood pump in the following. The pump function of the second pump 11 thereby normally takes over a centrifugal pump that is comprised of a pump drive and a pump head 12 driven without contact via a magnetic coupling. Additional suitable pumps would be rotary pumps such as semi-axial pumps (also designated as diagonal pumps). The pump head 12, which may also be designated in the following as a blood pump head, is connected to a supply line 13. Liquid—for example, blood from a patient—arrives via the supply line 13 into the gas exchange device 1. In a downstream course of the blood pump 11, the second fluid (thus, presently, the blood) is directed via a second line 14 into a gas exchanger 40, depicted as a mixing chamber. After the passage through the gas exchanger 40, the second fluid is directed via a discharge 16 back to a patient. What is known as an in-line pressure sensor 15 is additionally formed in the supply line 13. The pressure sensor 15 allows the determination of a pressure of the fluid—here, of blood—in the supply line 13, and thus, at least indirectly, also allows the determination of a flow rate toward the second pump 11. In addition to this, the pressure sensor 15 allows a determination of what is known as the drainage pressure, i.e., the pressure between the vascular access and the pump head 12 of the blood pump 11. More than one pressure sensor 15 may be provided, e.g., three pressure sensors 15. A pressure sensor prior to the pump 11, a pressure sensor between the pump 11 and the gas exchanger 40, and a pressure sensor after the gas exchanger 40 in the flow direction. The supply line 13, the blood pump 11, the second line 14, and the discharge line 16 are part of a second gas exchange section. The total length of the lines of the second fluid or blood is preferably less than 100 cm—more preferably, between 50 and 80 cm. The line or hose path outside of the housing 2, from and to the patient, is between 0.9 and 1.7 m—preferably, between 1 and 1.6 m.

The first pump 20 is designed as a gas pump. For this, in the embodiment shown in FIG. 1, the first pump 20 has two gas supply hoses 21. The gas supply hoses 21 serve to supply the pumping system 10 and the gas exchange device 1 as a whole with the gas that interacts with the liquid, conveyed by the second pump 11, in the gas exchanger 40. The gas supply hoses 21 thus form a part of a first gas exchange section of the gas exchange device 1. The gas supply lines 21 are spatially arranged in the gas exchange device 1 such that they travel in spatial proximity to the second pump 11—here, at least in sections. The waste heat of the second pump 11 may thereby warm the gas flowing in the gas supply lines 21.

The gas used in the first gas exchange section in this embodiment may, in particular embodiments, also be a liquid, such that, here, a fluid is also generally spoken of. In the shown embodiment, the gas is, in particular, ambient air, i.e., a known composition of various gases of breathable air that, in particular, has only a small proportion of $CO_2$.

The first pump 20 conveys the gas through a gas exchange line 24, 24a to the gas exchange section 40 of the gas exchange device 1, which forms the mixing chamber. In the shown embodiment, the gas is thereby initially directed through a gas flow sensor 22. This may therefore also allow a determination of the quantity of inflowing gas and its flow rate. The gas is directed through a particle filter 23 after passing through the gas flow sensor 22. The particle filter 23 is designed such that solid components, such as dust, pollen, or additional airborne particles or contaminants, are filtered out of the gas flow. The particle filter 23 may also be arranged at a different position of the formed first gas exchange section, e.g., already upstream of the gas flow sensor 22—in particular, also upstream of the first pump 20. It is also conceivable that a plurality of filters is formed at various positions of the first gas exchange section. Given a plurality of filters, a filter system may be provided that successively filters out particles of different sizes. It may thus be achieved that a probability of clogging of the first gas exchange section is at least reduced.

The gas that flows through the gas exchanger 40 flows again through the first pump 20. For this, in preferred embodiments, the first pump 20 is designed as a suction pump. The first pump 20 thereby draws the gas flow through the entire first gas exchange section, up to the outlet line 25. While such a suction pump conveys the gas flow through the gas exchanger 40 by means of a negative pressure, in alternative embodiments, it is also conceivable that the first pump 20 is an overpressure pump. The gas flow would thereby accordingly be conveyed through the gas exchanger or the mixing chamber 40 by means of a negative pressure.

The outlet line 25 is thereby downstream of the first pump 20. In addition to this, a noise suppressor 26 is provided between an outlet (not apparent in FIG. 1) and the first pump 20. The noise suppressor 26 is designed to dampen the noise level of the gas flow exiting from the outlet, and thus to reduce noise emission of the gas exchange device 1.

In the embodiment shown in FIG. 1, a blood flow and air bubble sensor 31 is furthermore designed in the second fluid circuit or in the second gas exchange section.

The actual gas exchange between the liquid (here, preferably, blood) and the fluid (here, preferably, ambient air) takes place in the gas exchanger 40, as is known from the prior art. According to a special embodiment of the present invention, only a decarboxylation without simultaneous oxygenation is to be performed with the device according to the invention. According to the invention, the components of the pumping system 10, as well as the associated components—such as gas exchanger 40, supply and discharge lines 13, 14, 16; 21, 24, 24a, 25, and additional components—are designed for volume flows in a range of less than 2 l/min—preferably, in a range of approx. 0.3-1 l/min. In addition to this, the components are dimensioned such that extracorporeal volumes, e.g., extracorporeal blood volumes, are kept low. In order to ensure a sufficient through-flow and an effective gas exchange at the low volume flows according to the invention, a fiber bundle having a plurality of individual hollow fibers, for example, is provided in the gas exchanger 40. Usable fiber bundles that may be connected to the gas and blood inflows and drains are already known from the prior art and are not described at this point.

Figure 2:
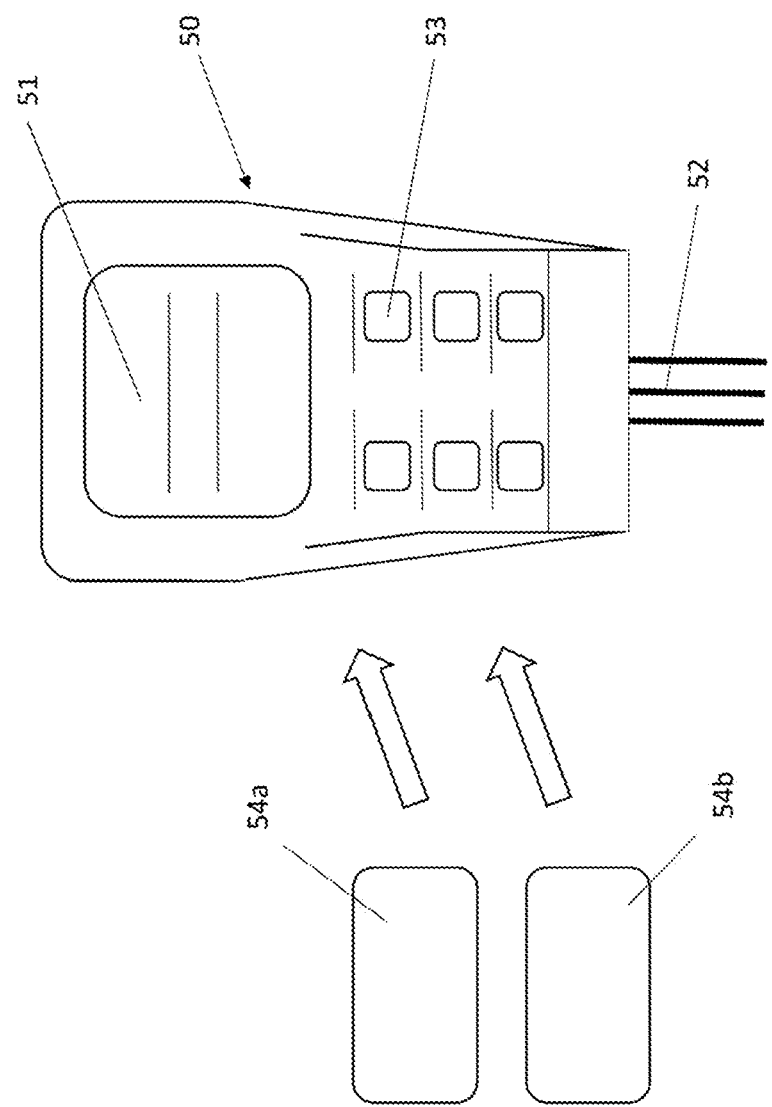
FIG. 2 is a view of an example of a control unit according to an embodiment of the invention.

The gas flow sensor 22 may be connected to a control device 50 of the gas exchange device 1, which is shown as an example in FIG. 2. The gas flow sensor may be connected to the second pump 20 and/or to the first pump 11. The pressure sensor 15 and/or the second pump 11 may be connected to the control unit 50. In this way, a control loop may be achieved for regulation of the gas flow rate and/or of the blood flow rate, or, in general, of the fluid flow rate and/or of the liquid flow rate. It is understood that it is also conceivable to create only a control switch loop, without a governor loop.

In the shown embodiment, the control device 50 has a display unit 51. In this shown embodiment, it is provided that the display unit 51 present a variety of information such as blood flow rate, gas flow rate, or pumping capacity of the pumps 11, 20 contained in the gas exchange device 1. A plurality of lines 52 is provided at the control unit 50. The lines 52 thereby include data lines from and to the various modules (such as sensors and pumps) in the gas exchange device. In addition to this, at least one of the lines 52 may serve to supply power to the control unit 50.

Furthermore, the control unit 50 has a plurality of control keys 53. For example, the control keys allow the selection and modification of various parameters that are relevant to the control or regulation of the gas exchange device 1.

In the shown embodiment, two rechargeable batteries 54a, 54b are provided in the control unit 50. These batteries 54a, 54b and the control unit 50 are thereby designed such that a supply of power to the control unit may also take place exclusively via one of the batteries. In this way, spatial proximity to an external power supply is not necessary at any point in time. Moreover, this design allows for one of the batteries 54b to be removed from the control unit 50 and, for example, recharged again while the other battery 54a remains in the control unit 50 and supplies this, as well as the corresponding components of the gas exchange device 1, with power. In addition to this, in a state in which the batteries are inserted into the control unit, charging of the batteries may also take place via the power supply of the control unit.

The housing 2 of the gas exchange device 1 preferably has a maximum internal chamber volume of preferably 9,500 $cm^3$, given a preferably maximum average depth (extent of the housing 2 in the direction orthogonal to the figure plane in FIG. 1) of 15 cm and given a preferred average total value of, altogether, at most, 65 cm for height and width. The average height or the average width hereby preferably amounts to 40 cm at most. The depth thereby preferably amounts to ¼ to ⅛ of the sum value of the average height and the average width taken together, such that the housing 2 achieves a compact—up to flat—character.

The gas exchange device also has a device for active temperature control. This comprises at least one temperature sensor 63 arranged in the housing 2, at least one ventilating fan 60, as well as a governor device that is integrated into the control device 50. The ventilating fan 60 is arranged in the housing 2, between a housing opening 62 and the second pump 11. The ventilating fan 60 is preferably arranged at a small distance of <3 cm from both the pump and the housing opening in the housing 2. In the housing 2, via the ventilating fan 60, an air flow may be generated, whose circulation between the two or more provided housing openings 61 and 62 is indicated by the arrows 64. By means of the device for active temperature control, in the operating state, the internal temperature in the housing 2 may be adjusted within a temperature range of 34 to 42° C.—preferably, in a temperature range of 35 to 38° C. The waste heat of the pumps 11, 20 is thereby distributed via the air current in the housing to warm the components, and excess heat may be delivered to the environment via the housing opening 62. The ventilating fan may thereby be operated in different flow directions in order to either distribute more heat in the housing or to discharge heat from the housing more quickly. In FIG. 1, the flow direction for rapid heat transport out of the housing is indicated via the arrows 64. The opposite flow or ventilation direction would produce a greater distribution of heat in the housing. If the patient to be treated must be "cooled," a target temperature lower than 35° C. is thus also possible.

The housing 2 is provided and prepared for accommodating the components of the first gas exchange section and of the second gas exchange section. For this, the housing 2 may have a plurality of recesses in a housing insert. The recesses are dimensioned such that the corresponding components of the gas exchange segments may be accommodated with positive fit in the recesses in the housing insert. In this way, a secure accommodation of the components of the gas exchange segments may take place, so that, in particular, relative movements, wear, and the release of connections may be effectively reduced.

The housing 2 may have a housing insert that features receptacle sections—in particular, for the first and second pumps 20, 11, the mixing chamber 40, and the supply and discharge lines of the fluid circuits and the like. In this way, in this shown embodiment, noise and temperature insulation may already take place. The housing insert is dimensioned such that this can be inserted with a precise fit into the housing.

REFERENCE LIST

1 Gas exchange device
2 Housing
2a Housing recesses
2b Housing insert
10 Pumping system
11 Second pump
12 Pump head
13 Fluid supply line
14 Second line
15 In-line pressure sensor
16 Fluid discharge line
20 First pump
21 Gas supply hose/fluid inflow line
22 Gas flow sensor
23 Particle filter
24/24a Gas exchange line
25 Fluid outlet line
26 Noise suppressor
31 Blood flow and air bubble sensor
40 Gas exchanger/mixing chamber
50 Control device
52 Lines
53 Control keys
54a/54b Rechargeable batteries
60 Ventilating fan
61 Housing opening
62 Housing opening
63 Temperature sensor
64 Arrows

The invention claimed is:

1. A portable gas exchange device for gas exchange of at least one gas with a fluid, comprising:
   a housing configured to be transported on a patient's body, the housing enclosing an internal chamber;
   a first gas exchange section for passage of a first fluid, the first fluid being gaseous;
   a second gas exchange section for passage of a second fluid comprising liquid enriched with a first gas, wherein the second fluid has a lower or higher concentration of the first gas than the first fluid;
   a pumping system disposed entirely in the internal chamber of the housing, the pumping system comprising a first gas pump for pumping the gaseous first fluid through the first gas exchange section and a second pump for pumping the second fluid through the second gas exchange section; and
   a mixing chamber disposed entirely in the internal chamber of the housing, the mixing chamber having a wall which is permeable at least to the first gas, the first gas exchange section and the second gas exchange section disposed in the mixing chamber and adjoining one another, separated by the wall.

2. The portable gas exchange device according to claim 1, wherein the first gas exchange section comprises a particle filter and wherein the gaseous first fluid essentially is ambient air, oxygen, or a mixture of ambient air and oxygen.

3. The portable gas exchange device according to claim 1, wherein, in the pumping system, the first gas pump and/or the second pump has a control for controlling the flow rate of the respective fluid.

4. The portable gas exchange device according to claim 3, wherein the flow rate of the first gas pump is adjustable to between 1-12 liters/min.

5. The portable gas exchange device according to claim 3, wherein the flow rate of the second pump is less than 2 liters/min.

6. The portable gas exchange device according to claim 1, wherein the first gas pump is a pump having a power-to-weight ratio of less than 30 kg/KW at a maximum pump weight of 0.5 kg.

7. The portable gas exchange device according to claim 1, wherein the second pump is a pump having a power-to-weight ratio of less than 25 kg/KW at a maximum pump weight of 0.7 kg.

8. The portable gas exchange device according to claim 1, wherein the ratio of the flow rates of the first gas pump to the second pump is in a range of between 4:1 and 6:1.

9. The portable gas exchange device according to claim 1, wherein the gas exchange device has a heating device for warming the gaseous first fluid and/or for keeping the second fluid warm.

10. The portable gas exchange device according to claim 9, wherein the heating device is provided such that a drive of the first gas pump and/or a drive of the second pump are positioned in the housing of the gas exchange device, such that a waste heat of the drive of the first gas pump and/or second pump warms an inlet-side section of a first fluid circuit and/or of a second fluid circuit.

11. The portable gas exchange device according to claim 1, further comprising a device for active temperature control that has at least one temperature sensor arranged in the housing, at least one ventilating fan, and a governor device.

12. The portable gas exchange device according to claim 11, wherein the ventilating fan is disposed between one of the pumps and a housing opening.

13. The portable gas exchange device according to claim 1, further comprising a noise suppressor for dampening a noise emission at an outlet side of a first fluid circuit.

14. The portable gas exchange device according to claim 1, wherein the gas exchange device further comprises at least either a pressure sensor and/or a gas flow sensor and/or an air bubble sensor.

15. The portable gas exchange device according to claim 1, wherein the first gas pump is a suction gas pump.

16. The portable gas exchange device according to claim 1, wherein the gas exchange device comprises an autarkic fluid supply for supplying the gas exchange device with the fluid.

17. The portable gas exchange device according to claim 1, further comprising a control unit adapted to control the flow rate of at least one pump of the pumping device.

18. The portable gas exchange device according to claim 1, wherein the wall between the first gas exchange section and the second gas exchange section is permeable to at least one second gas.

19. The portable gas exchange device according to claim 1, wherein the liquid of the second fluid is blood.

20. The portable gas exchange device according to claim 1, wherein the second pump is a centrifugal pump.

21. The portable gas exchange device according to claim 20, wherein the centrifugal pump comprises a pump drive and a pump head, the pump drive driving the pump head through a contactless magnetic coupling.

22. The portable gas exchange device according to claim 1, wherein:
the first gas exchange section further comprises a gas supply line for inflow of gas;
the first gas pump and second pump are adjacent to one another; and
the gas supply line is disposed between the first gas pump and second pump.

23. The portable gas exchange device according to claim 1, wherein:
the first gas exchange section further comprises a gas supply line for inflow of gas;
the second gas exchange section further comprises a fluid supply line for inflow of fluid; and
the gas supply line and the fluid supply line enter the housing on opposite sides of the housing.

24. The portable gas exchange device according to claim 1, wherein the gaseous first fluid is ambient air and the portable gas exchange device is not attached to a bottle of gas.

25. A portable gas exchange device for gas exchange of at least one gas with a fluid, comprising:
a housing configured to be transported on a patient's body, the housing enclosing an internal chamber;
a first gas exchange section for passage of a first fluid, the first fluid being gaseous;
a second gas exchange section for passage of a second fluid comprising liquid enriched with a first gas, wherein the second fluid has a lower or higher concentration of the first gas than the first fluid;
a pumping system disposed entirely in the internal chamber of the housing, the pumping system comprising a first gas pump for pumping the gaseous first fluid through the first gas exchange section and a second pump for pumping the second fluid through the second gas exchange section;
a mixing chamber disposed entirely in the internal chamber of the housing, the mixing chamber having a wall which is permeable at least to the first gas, the first gas exchange section and the second gas exchange section disposed in the mixing chamber and adjoining one another, separated by the wall; and
an active temperature control having at least one temperature sensor arranged in the internal chamber of the housing, at least one ventilating fan, and a governor device, the active temperature control configured to maintain a temperature in the internal chamber of the housing in a range of 34 to 42 degrees Celsius.

* * * * *